US00PP18831P3

(12) United States Plant Patent
Schräder

(10) Patent No.: US PP18,831 P3
(45) Date of Patent: May 27, 2008

(54) *PLECTRANTHUS* PLANT NAMED 'SUMCOL 03'

(50) Latin Name: *Plectranthus*
Varietal Denomination: Sumcol 03

(76) Inventor: Ralf Schräder, Lüdinghausen (DE)

( * ) Notice: Subject to any disclaimer, the term of this patent is extended or adjusted under 35 U.S.C. 154(b) by 0 days.

(21) Appl. No.: 11/480,204

(22) Filed: Jun. 30, 2006

(65) Prior Publication Data

US 2008/0005819 P1 Jan. 3, 2008

(51) Int. Cl.
*A01H 5/00* (2006.01)

(52) U.S. Cl. ..... Plt./373

(58) Field of Classification Search ..... Plt./373
See application file for complete search history.

*Primary Examiner*—Kent Bell
(74) *Attorney, Agent, or Firm*—The Webb Law Firm

(57) ABSTRACT

A *Plectranthus* plant named 'Sumcol 03' particularly characterized by its strong fragrance and compact, rounded shape. The plant has shown resistance to botrytis, snails, and caterpillars. Animals, such as cats and dogs, avoid the present plant because of its strong fragrance.

1 Drawing Sheet

Botanical classification: *Plectranthus* hybrid.
Varietal denomination: 'Sumcol 03'.

BACKGROUND OF THE INVENTION

The present invention comprises a new and distinct cultivar of *Plectranthus* hybrid known by the varietal name 'Sumcol 03'.

The new cultivar was discovered in a cultivated area as a naturally occurring and spontaneous branch mutation of *Plectranthus* hybrid 'Sumcol 01' (U.S. Plant Pat. No. PP13, 843). The new variety was discovered in June of 2002 in Lüdinghausen, Germany.

'Sumcol 03' has a similar fragrance to 'Sumcol 01', but has different colored leaves.

The first asexual reproduction of the new variety took place in Lüdinghausen, Germany in August 2002 by cuttings. Continued observations of the vegetative cuttings have confirmed that the distinguishing features of the new cultivar remain stable and true to type through successive asexual propagations.

DESCRIPTION OF THE DRAWING

The accompanying photographic drawing illustrates the new cultivar, the color being as nearly true as possible with color illustrations of this type.

DESCRIPTION OF THE NEW PLANT

Figure 1:
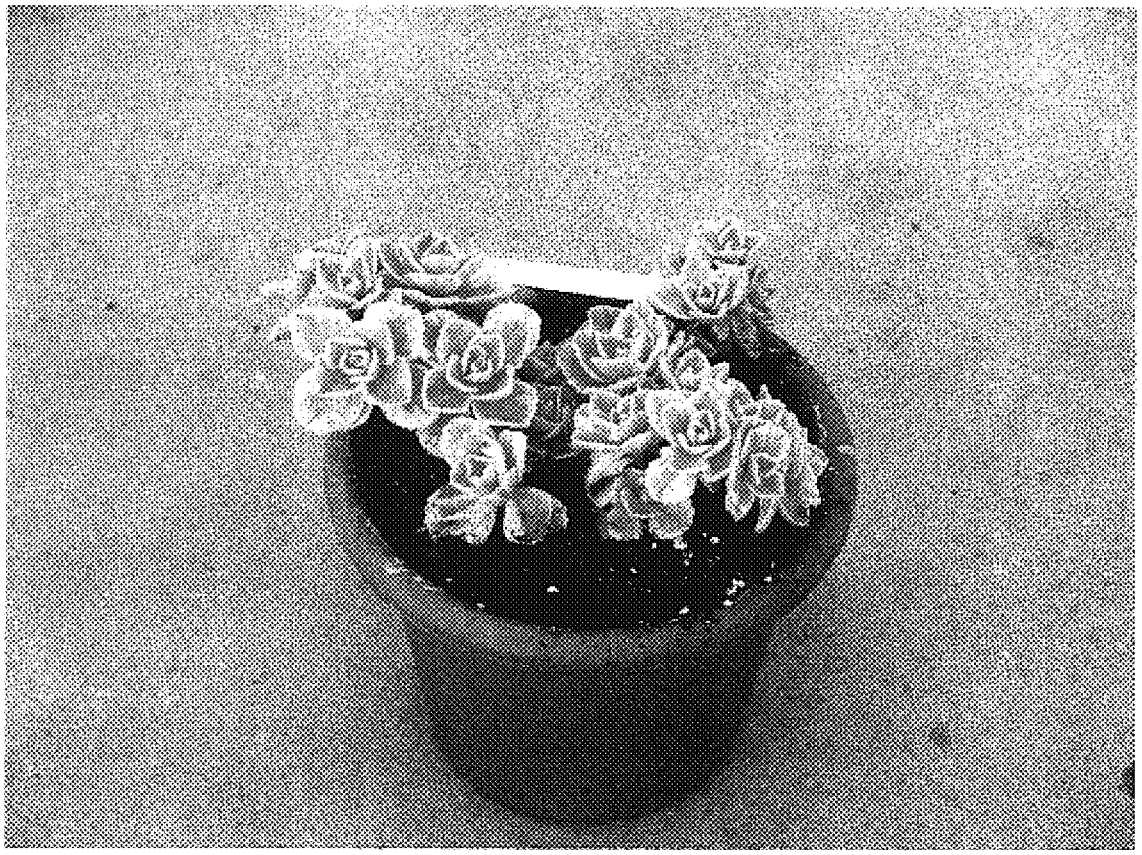

The following detailed description sets forth the characteristics of the new cultivar. The data which defines these characteristics was collected indoors in Lüdinghausen, Germany on a partly cloudy day. Color references are primarily to the 2001 R.H.S. Colour Chart of The Royal Horticultural Society of London except where general terms of ordinary dictionary significance were used.

PLANT

Height: 25 cm.
Width: 30 cm.
Form: Compact, rounded.
Stems:
- *Length.*—21 mm.
- *Diameter.*—8–10 mm.
- *Surface texture.*—Fleshy.
- *Color.*—199A.

Branches:
- *Length.*—30 cm.
- *Diameter.*—18 mm.
- *Surface texture.*—Fleshy.
- *New growth color.*—144B.
- *Mature growth color.*—199A.
- *Internode length.*—10.5 mm.

Leaves:
- *Length.*—35 mm.
- *Width.*—33 mm.
- *Apex.*—Acute.
- *Base.*—Rotundate.
- *Margin.*—Crenate.
- *Surface texture.*—Rippled.
- *Shape.*—Obovate.
- *Color.*—Upper surface: 157B around the border, with 139D in the interior and 191B in the center. Lower surface: 191A.
- *Mid-vein.*—Size: 17 mm. Color: 145C.
- *Petioles.*—Length: 12 mm. Diameter: 2–3 mm. Thickness: Moderate. Color: 145B.

Growing conditions: The new cultivar is preferably cultivated in peat soil at a pH between 5.5 and 6.0. The natural flowering period is summer. Freezing temperatures are fatal to the new cultivar.

Disease/pest resistance: Resistant to botrytis, snails, and caterpillars.

Other features: Like 'Sumcol 01', cats and dogs avoid the present cultivar because of its strong fragrance.

INFLORESCENCE

Peduncles:
*Color.*—145A.
*Length.*—80 mm.
*Diameter.*—12–15 mm.
Buds:
*Shape.*—Spike.
*Length.*—40 mm.
*Diameter.*—15–20 mm.
*Color.*—147A.
Flowers:
*Type.*—Paniculate.
*Length.*—80 mm.
*Diameter.*—16 mm.
*Average number of blooms per cluster.*—20 to 30.
*Form.*—Single to bilabiate.
*Color when opening begins, in bloom, and end of bloom.*—Upper and lower surfaces: 97B.
*Fragrance.*—Unpleasant.
*Petals.*—Form: Ovial and labiate. Number: Two. Lasting quality: 5 to 8 days from opening to end of life. Sepals: Number per flower: 2. Length: 22 mm. Width: 6 mm. Shape: Lanceolate. Apex: Pointed. Base: Round. Margin: Entire. Upper surface color: N88C. Lower surface color: 85D.

REPRODUCTIVE ORGANS

Sexual characteristics: Bisexual.
Pistil number per flower: 1.
Ovary:
*Shape.*—4 small ovals in cruciform.
*Length.*—1 mm.
*Width.*—1 mm.
*Color.*—153D.
Style:
*Length.*—20–23 mm.
*Color.*—N89B.
Stamen:
*Number per flower.*—4.
*Length.*—20 mm.
*Shape.*—Round.
*Color.*—N89B.

FRUIT

Maturity date: 21 days from crossing until fruit produced.
Size: Approximately 0.5 mm.
Shape: Round; uniform.
Color: 200A.
Flesh texture: Hard.

I claim:

1. A new and distinct variety of *Plectranthus* plant as is herein described and illustrated.

* * * * *